(12) United States Patent
Gibson et al.

(10) Patent No.: US 10,850,058 B2
(45) Date of Patent: Dec. 1, 2020

(54) MASK SYSTEM

(71) Applicant: ResMed Pty Ltd, Bella Vista, New South Wales (AU)

(72) Inventors: Joel Edward Gibson, Sydney (AU); Justin John Formica, Sydney (AU); Adam Francis Barlow, Sydney (AU); Jessica Lea Dunn, Sydney (AU); Jose Ignacio Romagnoli, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 260 days.

(21) Appl. No.: 15/973,574

(22) Filed: May 8, 2018

(65) Prior Publication Data

US 2018/0256845 A1    Sep. 13, 2018

Related U.S. Application Data

(63) Continuation of application No. 13/817,370, filed as application No. PCT/AU2011/001129 on Aug. 31, 2011, now Pat. No. 9,993,606.

(60) Provisional application No. 61/344,621, filed on Sep. 1, 2010.

(51) Int. Cl.
*A61M 16/06* (2006.01)
*A61M 16/08* (2006.01)

(52) U.S. Cl.
CPC .... *A61M 16/0683* (2013.01); *A61M 16/0605* (2014.02); *A61M 16/0616* (2014.02); *A61M 16/0816* (2013.01); *A61M 2207/00* (2013.01)

(58) Field of Classification Search
CPC .............. A61M 16/06; A61M 16/0605; A61M 16/0611; A61M 16/0616; A61M 16/0622; A61M 16/0683; A61M 16/08; A61M 16/0816; A61M 16/0875
See application file for complete search history.

(56) References Cited

U.S. PATENT DOCUMENTS

| | | |
|---|---|---|
| 3,101,709 A | 8/1963 | Gruenewaelder |
| 4,300,240 A | 11/1981 | Edwards |
| 4,458,679 A | 7/1984 | Ward |
| 4,790,307 A | 12/1988 | Haber et al. |
| 4,809,692 A | 3/1989 | Nowacki et al. |

(Continued)

FOREIGN PATENT DOCUMENTS

| | | |
|---|---|---|
| CA | 2 744 637 A1 | 6/2001 |
| CN | 1901962 | 1/2007 |

(Continued)

OTHER PUBLICATIONS

Extended European Search Report dated Dec. 14, 2018 in European Application No. 18178389.5 (8 pages).

(Continued)

*Primary Examiner* — Joseph D. Boecker
(74) *Attorney, Agent, or Firm* — Nixon & Vanderhye P.C.

(57) ABSTRACT

A mask system including a headgear and cushion module and a seal and frame module provided to the headgear and cushion module. The seal and frame module includes a sealing portion adapted to form a seal with the patient's face and a frame portion adapted to form a breathing chamber. The headgear and cushion module includes a cushion region adapted to support and shape the sealing portion and a headgear region adapted to support and stabilize the mask system on the patient's face.

20 Claims, 15 Drawing Sheets

(56) References Cited

U.S. PATENT DOCUMENTS

| | | | |
|---|---|---|---|
| 5,053,271 A | 10/1991 | Mori et al. | |
| 5,322,060 A | 6/1994 | Johnson | |
| 5,372,130 A | 12/1994 | Stern et al. | |
| 5,538,000 A * | 7/1996 | Rudolph | A61M 16/06 128/201.22 |
| 5,709,204 A | 1/1998 | Lester | |
| 5,884,336 A | 3/1999 | Stout | |
| 6,371,110 B1 | 4/2002 | Peterson | |
| 6,467,482 B1 | 10/2002 | Boussignac | |
| 6,659,102 B1 | 12/2003 | Sico | |
| 6,698,427 B1 | 3/2004 | Clowers | |
| 6,718,982 B2 | 4/2004 | Smith et al. | |
| 7,640,933 B1 | 1/2010 | Ho | |
| 8,132,270 B2 | 3/2012 | Lang et al. | |
| 9,162,034 B2 | 10/2015 | Veliss | |
| 9,981,104 B1 * | 5/2018 | Groll | A61M 16/0816 |
| 9,993,606 B2 * | 6/2018 | Gibson | A61M 16/0683 |
| 2002/0023647 A1 | 2/2002 | Hansen | |
| 2005/0121030 A1 | 6/2005 | Bateman | |
| 2005/0284481 A1 * | 12/2005 | Meyer | A61M 16/06 128/207.11 |
| 2006/0011201 A1 | 1/2006 | Ku | |
| 2006/0085881 A1 | 4/2006 | Gellis | |
| 2006/0102184 A1 * | 5/2006 | Kullik | A61M 16/06 128/206.24 |
| 2006/0118119 A1 | 6/2006 | Berthon-Jones et al. | |
| 2007/0175479 A1 * | 8/2007 | Groll | A61M 16/0683 128/206.24 |
| 2007/0246043 A1 * | 10/2007 | Kwok | A61M 16/0666 128/201.22 |
| 2008/0047560 A1 * | 2/2008 | Veliss | A61M 16/06 128/206.24 |
| 2008/0060649 A1 * | 3/2008 | Veliss | A61M 16/0683 128/205.25 |
| 2008/0142015 A1 | 6/2008 | Groll | |
| 2008/0205683 A1 | 8/2008 | Weyer | |
| 2008/0295845 A1 | 12/2008 | Nashed | |
| 2009/0044808 A1 * | 2/2009 | Guney | A61M 16/0605 128/206.24 |
| 2009/0199856 A1 | 8/2009 | Berlin | |
| 2009/0242529 A1 | 10/2009 | Groll et al. | |
| 2010/0018534 A1 | 1/2010 | Veliss | |
| 2010/0024826 A1 | 2/2010 | Sullivan | |
| 2010/0319700 A1 | 12/2010 | Ng | |
| 2011/0146685 A1 | 6/2011 | Allan | |
| 2011/0197341 A1 | 8/2011 | Formica | |
| 2011/0247628 A1 | 10/2011 | Ho | |
| 2011/0253144 A1 | 10/2011 | Groll | |
| 2012/0055485 A1 | 3/2012 | Anthony | |
| 2013/0074845 A1 | 3/2013 | Smith | |
| 2013/0139822 A1 | 6/2013 | Gibson et al. | |
| 2013/0152937 A1 | 6/2013 | Jablonski | |
| 2015/0128949 A1 * | 5/2015 | Jablonski | A61M 16/06 128/205.25 |
| 2017/0326320 A1 * | 11/2017 | Baigent | A61M 16/0683 |

FOREIGN PATENT DOCUMENTS

| | | |
|---|---|---|
| CN | 1901963 | 1/2007 |
| CN | 101229410 | 7/2008 |
| CN | 101237902 | 8/2008 |
| CN | 101330944 A | 12/2008 |
| CN | 101400409 A | 4/2009 |
| CN | 201426908 Y | 3/2010 |
| DE | 40 04 157 | 4/1991 |
| GB | 2 385 533 | 8/2003 |
| GB | 2 397 244 | 7/2004 |
| WO | WO 02/47749 | 6/2002 |
| WO | WO 2004/041342 A1 | 5/2004 |
| WO | WO 2005/118042 A2 | 12/2005 |
| WO | WO 2007/089553 | 8/2007 |
| WO | 2009/026627 A1 | 3/2009 |
| WO | WO 2009/052560 A1 | 4/2009 |
| WO | 2009/100905 A1 | 8/2009 |
| WO | WO 2009/105528 | 8/2009 |
| WO | WO 2010/066004 | 6/2010 |
| WO | WO 2010/073138 | 7/2010 |

OTHER PUBLICATIONS

Office Action dated Apr. 23, 2018 issued in Chinese Application No. 201510674166.6 with English translation (14 pages).
Further Examination Report dated Mar. 5, 2018 issued in New Zealand Application No. 729437 (2 pages).
Notification of Second Office Action dated Oct. 20, 2017 issued in Chinese Application No. 201510674166.6 with English translation (11 pages).
Office Action dated Mar. 20, 2017 issued in Chinese Application No. 201510674166.6 with English translation (13 pages).
Further Examination Report dated Mar. 29, 2017 issued in New Zealand Application No. 711508 (2 pages).
First Examination Report dated Mar. 16, 2017 issued in New Zealand Application No. 729437 (2 pages).
Communication dated Mar. 22, 2017 issued in European Application No. 11 820 924.6 (5 pages).
First Examination Report issued in corresponding New Zealand Application No. 711508 dated Sep. 22, 2015.
Extended European Search Report issued in corresponding European Appln. No. 11 82 0924.6 dated Apr. 28, 2015.
Office Action issued in corresponding Chinese Appln. No. 201180040946.5 dated Feb. 10, 2015, with English translation thereof.
First Examination Report issued in corresponding New Zealand Appln. No. 701943, dated Dec. 5, 2014.
Partial Supplementary European Search Report issued in corresponding EP 11 82 0924.6 dated Nov. 21, 2014.
Chinese Office Action issued in corresponding CN Appln. No. 201180040946.5 dated Sep. 4, 2014, with English translation thereof.
First Examination Report issued in a corresponding New Zealand Application No. 606558, dated Sep. 18, 2013.
International Search Report for Application No. PCT/AU2011/001129, dated Nov. 11, 2011.

\* cited by examiner

MASK SYSTEM

CROSS-REFERENCE TO APPLICATION

This application is a continuation of U.S. application Ser. No. 13/817,370, filed Feb. 15, 2013, now allowed, which is the U.S. national phase of International Application No. PCT/AU2011/001129, filed Aug. 31, 2011, which designated the U.S. and claims the benefit of U.S. Provisional Application No. 61/344,621, filed Sep. 1, 2010, each of which are incorporated herein by reference in their entirety.

FIELD OF TECHNOLOGY

The present technology relates to a mask system used for treatment, e.g., of Sleep Disordered Breathing (SDB) with Continuous Positive Airway Pressure (CPAP) or Non-Invasive Positive Pressure Ventilation (NIPPV).

BACKGROUND OF TECHNOLOGY

Patient interfaces, such as a full-face or nasal mask systems, for use with positive airway pressure (PAP) devices in the treatment of Sleep Disordered Breathing (SDB), typically include a soft face-contacting portion, such as a cushion, and a rigid or semi-rigid shell or frame. In use, the interface is held in a sealing position by headgear so as to enable a supply of air at positive pressure (e.g., 2-30 cm $H_2O$) to be delivered to the patient's airways.

One factor in the efficacy of therapy and compliance of patients with therapy is the comfort and fit of the patient interface.

The present technology provides alternative arrangements of mask systems to enhance the efficacy of therapy and compliance of patients with therapy.

SUMMARY OF TECHNOLOGY

One aspect of the disclosed technology relates to a mask system that is easy to fit, provides a low part count, provides low manufacturing cost, and/or provides high quality performance, e.g., seal.

Another aspect of the disclosed technology relates to a mask system including a headgear and cushion module and a seal and frame module provided to the headgear and cushion module. The seal and frame module includes a sealing portion adapted to form a seal with the patient's face and a frame portion adapted to form a breathing chamber. The headgear and cushion module includes a cushion region adapted to support and shape the sealing portion and a headgear region adapted to support and stabilize the mask system on the patient's face.

Another aspect of the disclosed technology relates to a mask system including a cushion and headgear module including a one piece construction having an outer fabric layer and an inner cushioning layer within the fabric layer. The cushion and headgear module includes a cushion region adapted to define a breathing chamber and form a seal with the patient's face and a headgear region including straps adapted to maintain the cushion region in position on the patient's face in use.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings.

DETAILED DESCRIPTION OF ILLUSTRATED EXAMPLES

Figure 1:
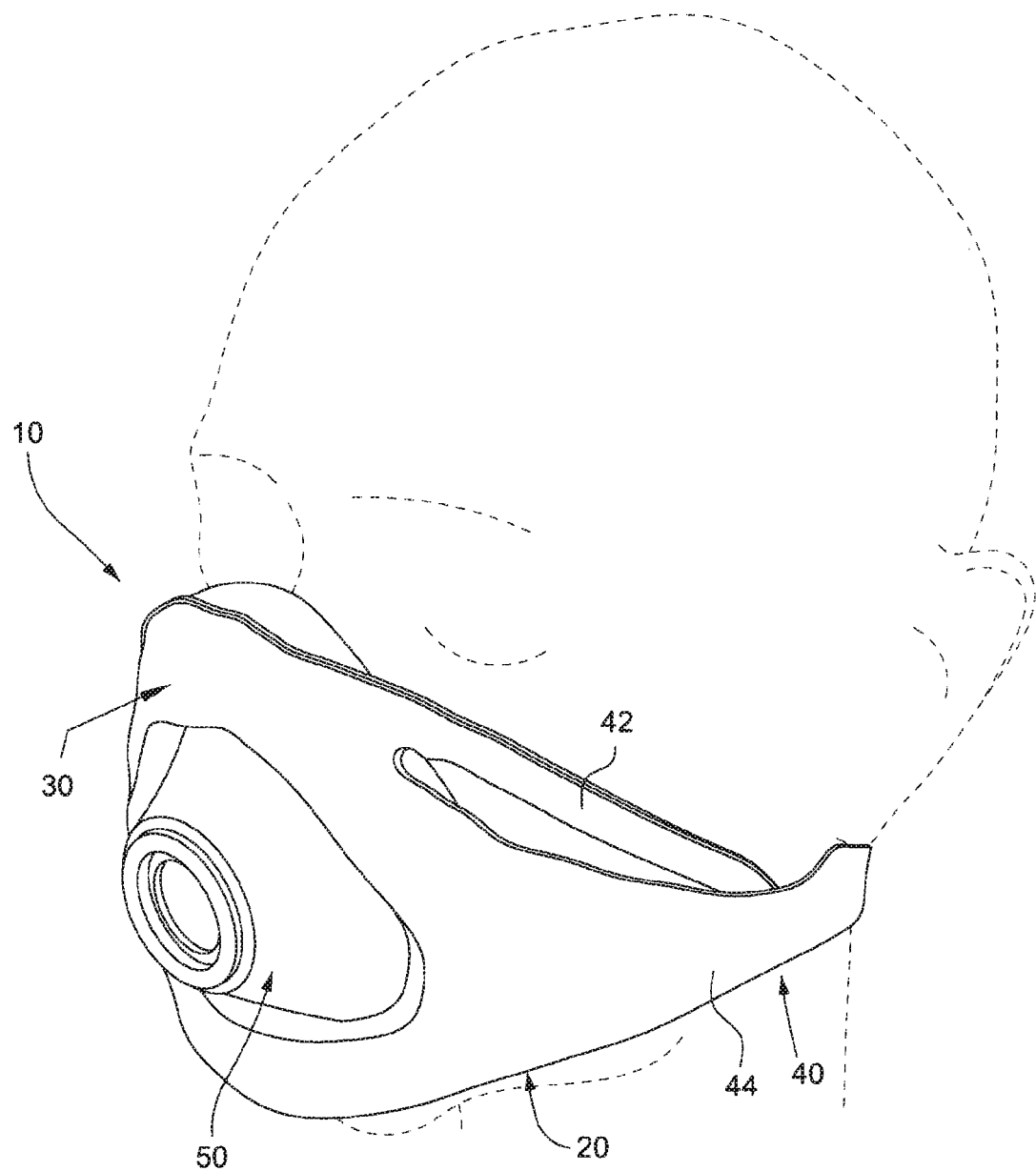
FIG. 1 is a perspective view of a mask system according to an example of the present technology, the mask system in position on a patient's head.

The following description is provided in relation to several examples (most of which are illustrated, some of which may not) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

Mask System

In the illustrated example, the full-face mask system 10 includes a headgear and cushion module 20 and a seal and frame module 50 provided to the headgear and cushion module. An elbow 90 may be provided to the seal and frame module 50 and adapted to be connected to an air delivery tube that delivers breathable gas to the patient. The mask system is intended for use in positive pressure therapy for users with Obstructive Sleep Apnea (OSA) or another respiratory disorder.

Exemplary advantages of the mask system 10 include a relatively low cost and a robust seal. For example, the relatively low cost may be provided by combining elements that would normally be multiple parts, e.g., headgear and cushion, and automated manufacturing. The robust seal may be provided by little to no air pressure to assist seal and/or comfort of the seal.

While each example below is described as including a full-face interface type, aspects of the present technology may be adapted for use with other suitable interface types, e.g., nasal interface, nasal prongs, etc.

1. Headgear and Cushion Module

The headgear and cushion module 20 includes a composite including an outer fabric or textile layer that provides an exterior surface of the module and an inner conformable, cushioning, and flexible layer or filler encapsulated or contained within the fabric layer. In an example, the fabric and filler (e.g., including cushioning and structural components) may include a single piece construction (e.g., made by laminating, heat pressing, welding, sewing, etc. components together). The one piece or integral construction of the headgear and cushion module provides fewer components which may be more consumer friendly. As described in greater detail below, the headgear and cushion module 20 includes a cushion region 30 and a headgear region 40.

In an example, the composite may be formed of a foam and a fabric, with the foam being completely encapsulated or contained within the fabric. The foam may be laminated to, insert molded on, compressed, or otherwise attached to the fabric. Alternatively, the foam may not be attached to the fabric but rather may be adjacent to it, e.g., foam inserted into a fabric sock.

The fabric may be coated or otherwise sealed to create an air impermeable seal. The fabric may be coated with a laminate, e.g., a silicone, polyurethane or other polymer sheet. Alternatively, the fabric may be spray coated with a polymer.

In an alternative example, the foam may be replaced by an alternative material, e.g., a spacer fabric. Preferably, the filler (i.e., foam, spacer fabric) may be conformable and flexible.

1.1 Cushion Region

Cushioning Component

Figure 4:
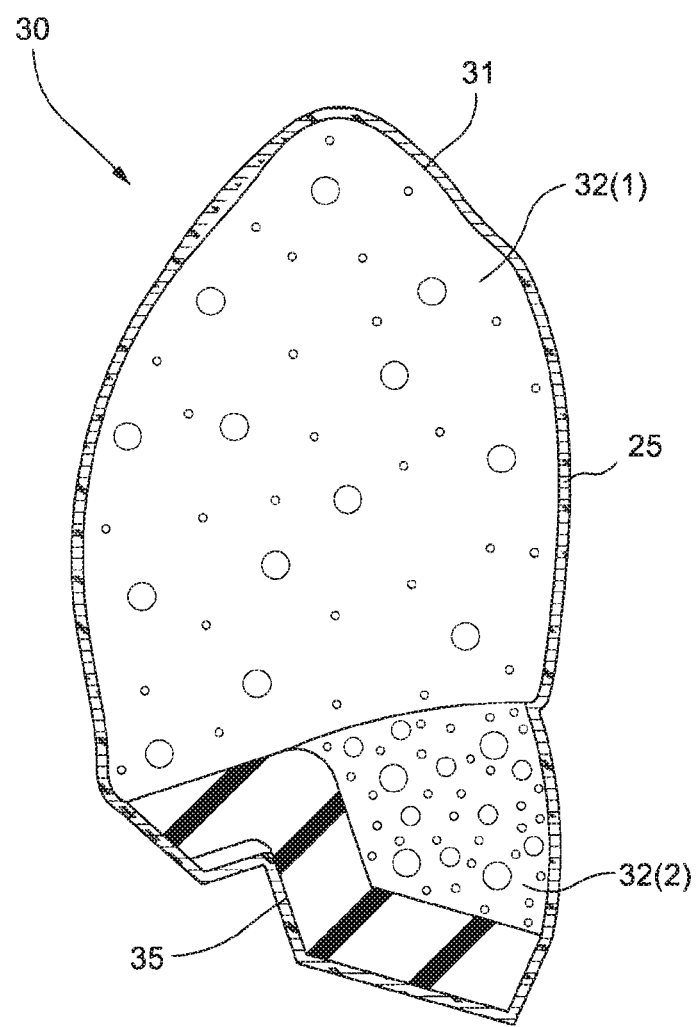
FIG. 4 is a cross-sectional view of a cushion region of a headgear and cushion module of the mask system shown in FIG. 1.

The cushion region 30 includes a cushioning component 31 within the fabric layer 25 (see FIG. 4). The cushioning component may be a conformable, flexible region that provides comfort for the patient. The cushioning component may also support and shape the sealing membrane 52 of the seal and frame module 50 (described below) when positioned on the patient's face in use. Preferably, the cushioning component is elastic or resilient such that it applies a reactive force when in use on the patient's face. Alternatively, the cushioning component may be visco-elastic.

Preferably, the cushioning component may include at least one layer or filler within the fabric layer. Preferably, at least one layer is a foam. The foam may be a silicone foam (e.g., biocompatible so suitable for use in the air path) or a polyurethane foam. Other materials that may be used include spacer fabric, gel, TPE or silicone. In a preferred example, there are two or more layers of foam forming the cushioning component, e.g., a first softer layer of foam 32(1) and second harder layer of foam 32(2) as shown in FIG. 4. The foams may differ in their chemical composition, densities, hardness, shape, visco-elasticity, elasticity, cell structure or any other property of the foam. In a preferred example, a first layer may be constructed from a foam with a hardness ILD @ 40% of less than 100N, e.g., 25-80N. A second layer may be constructed from a foam with a hardness ILD @ 40% of less than 100N, e.g., 25-80N. The layers of foam may be joined together by glue or may be co-molded.

Alternatively, the cushioning component may be an arrangement of one or more springs. Alternatively, the cushioning component may be a bladder or space filled with air or other flowable material, such as gel, oil, water. Alternatively, the cushioning component may be a bladder filled with beads or beans.

The cushioning component may be generally triangular, trapezoidal, oval, circular, trilobular, or any other shape such that when positioned on the face of the patient, it passes the nasal bridge region, cheek regions and either the chin or upper lip regions. The cushioning component may have a constant cross section or have a variable cross section.

Structural Component

As shown in FIG. 4, the cushion region 30 may also include a structural component 35 that provides support to the cushioning component 31 so that the cushion can be positioned so as to engage with the patient's face. The structural component (also referred to as a stiff element, rigid element, or rigidizer) may provide structural support to help prevent the cushion from flexing or bending out of contact with the patient's face. The structural component may be made from a silicone (preferably low durometer silicone so that the mask is flexible, for example 10-30 Shore A), TPE, polypropylene, polycarbonate, polyurethane. Alternatively, the structural component may be formed of a textile or foam that has been thermoformed or embossed to create a dense or stiffer section of textile or foam.

The structural component may influence the position of the cushion component. For example, the structural component may be curved, for example to the contours of a person's face, so that when in contact with the cushion component, the cushion is also curved. Furthermore, the structural component may be adjustable so that the patient can influence the position of the cushion component by altering the shape of the structural component. For example, the structural component may be a malleable wire.

The structural component may extend around the cushion component. Alternatively the structural component may only be in one or more regions of the cushion component; for example, there may be a structural component at the nasal bridge region of the cushion to support the seal as this area is prone to leak. If the structural component is adjustable, it may be adjustable in one or more regions of the structural component. For example, the structural component may be adjustable at the nasal bridge region so the patient can compress the cushion into position around their nose.

The structural component may be removably or fixedly connected to the cushion component by chemical (for example, glue, co-molding, overmolding) or mechanical means (for example, clip, interference fit, tongue and groove, hook and loop, magnetic).

However, it should be appreciated that the structural component may be optional, and it may be possible to utilize higher density foam, embossing, 3D weaves, spacer fabrics, etc. to provide stiffness to the cushioning component.

The structural component may have varying hardness or stiffness zones that may create regions having more support of the cushion component, and other regions having less support for the cushion component. For example, the structural component may have a lower stiffness at the nose bridge to accommodate varying nose bridge sizes, and may have a higher stiffness at the corners of the nose or chin region to ensure stability and anchoring of the cushion component at the boney regions of the face.

In an example, the structural component may be thermoformed within the fabric layer to assist in shaping the seal portion of the seal and frame module 50. The structural component may be an additional component, e.g. malleable wire or plastic strip, or may be a region of the foam having a stiffer or more rigid property than surrounding regions of the foam, i.e., the foam may be selectively stiffened in one more regions. Selective stiffening of the foam may be achieved by using different types of foams for different regions of the cushion, or by treating the foam in different regions to alter the properties of the foam, e.g., compress or heat press, cut holes in the foam.

Figure 13:
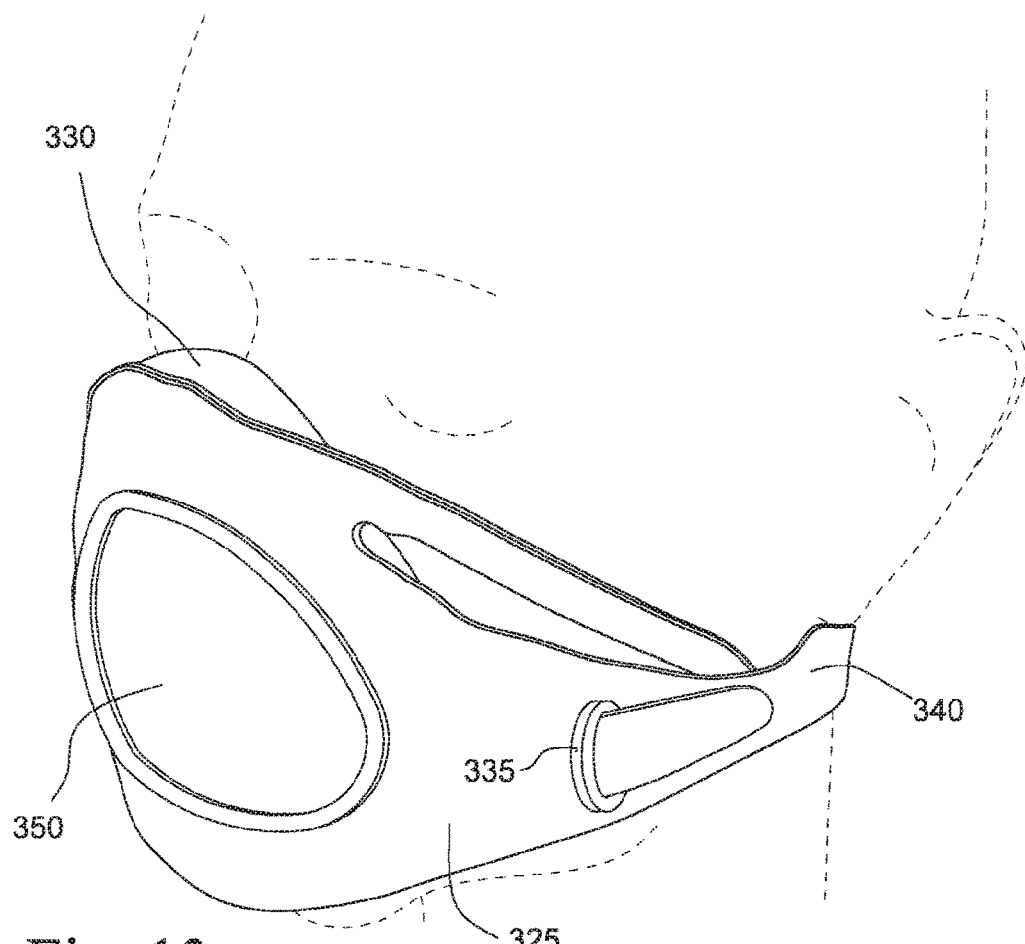
FIG. 13 is a perspective view of a mask system according to another example of the present technology, the mask system in position on a patient's head.

The structural component may extend outside of the outer fabric layer to enable connection of the structural component to external components. For example, as shown in FIG. 13, a mask having a cushion region 330 and a sealed region 350 (e.g., a sealed textile portion or polymer portion) may include a structural component 335 that may extend outside of an outer fabric layer 325 to form a headgear connection region adapted to receive a headgear strap 340.

Alternatively, the structural component may extend outside of the outer fabric to form a tube connection portion adapted to receive an air delivery tube. Such an arrangement may be desirable if the cushion and headgear component are air holding and/or deliver breathable gas to the patient.

1.2 Headgear Region

The headgear region 40 is used to support and stabilize the headgear and cushion module 30 on the face of the user. The headgear region preferably is positioned along the cheeks and under the ears of the patient extending to the back of the patient's neck in use, e.g., see FIG. 1. Alternative configurations are possible, e.g., over the ear, over the crown, etc.

Figure 2:
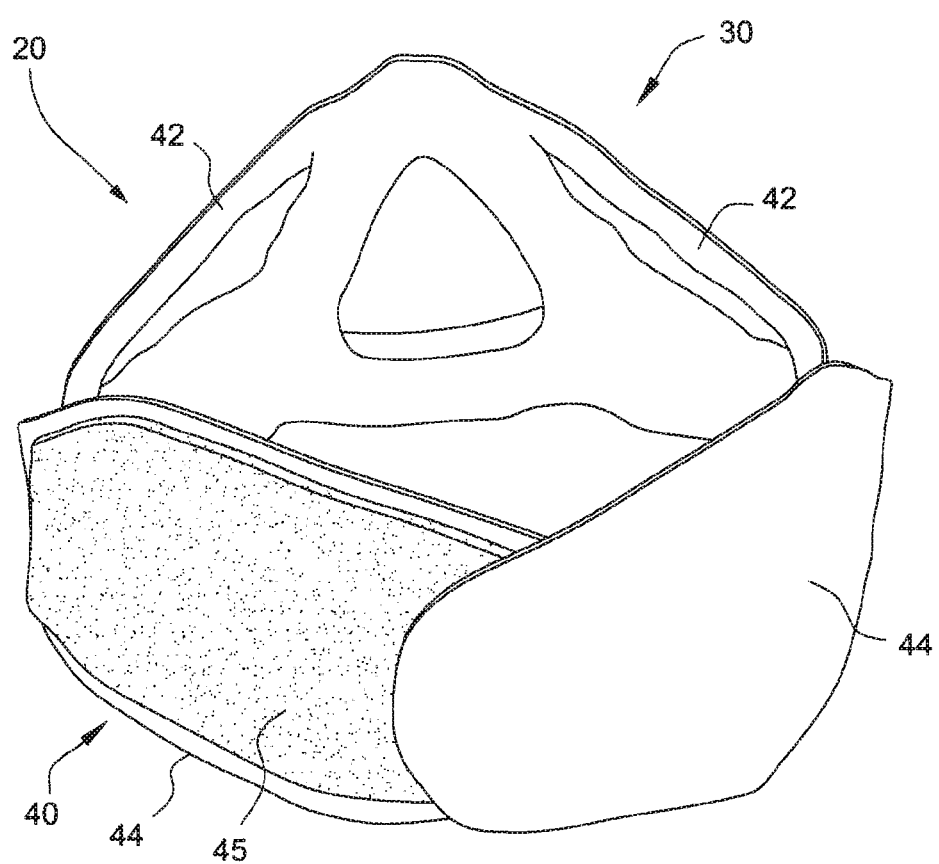
FIG. 2 is a perspective view of a headgear and cushion module of the mask system shown in FIG. 1.
Figure 3:
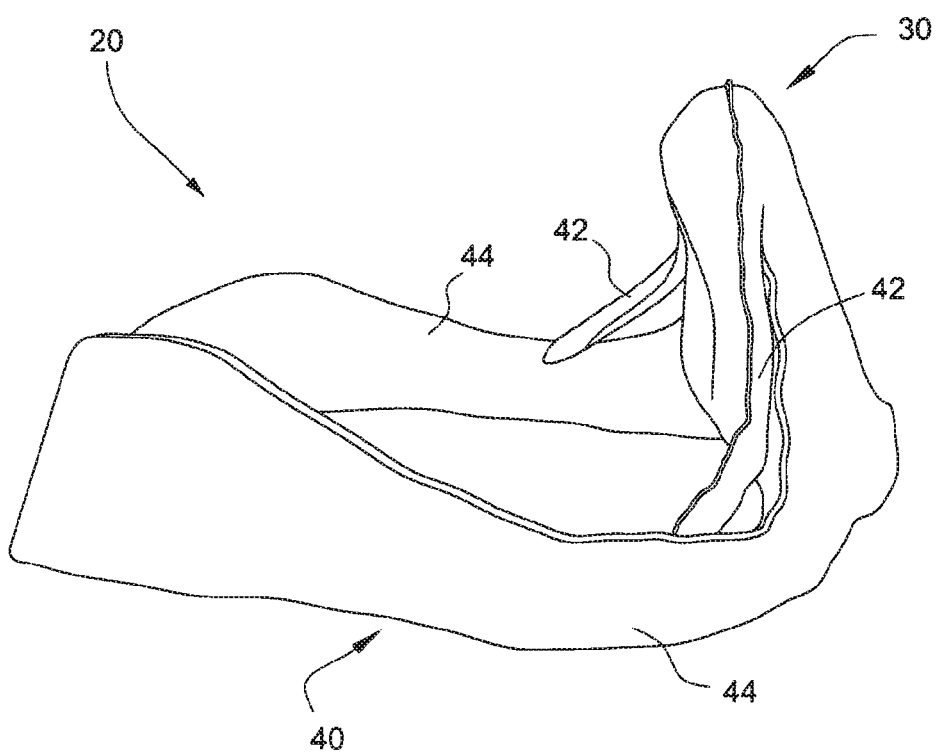
FIG. 3 is a side perspective view of a headgear and cushion module of the mask system shown in FIG. 1.
Figure 8:
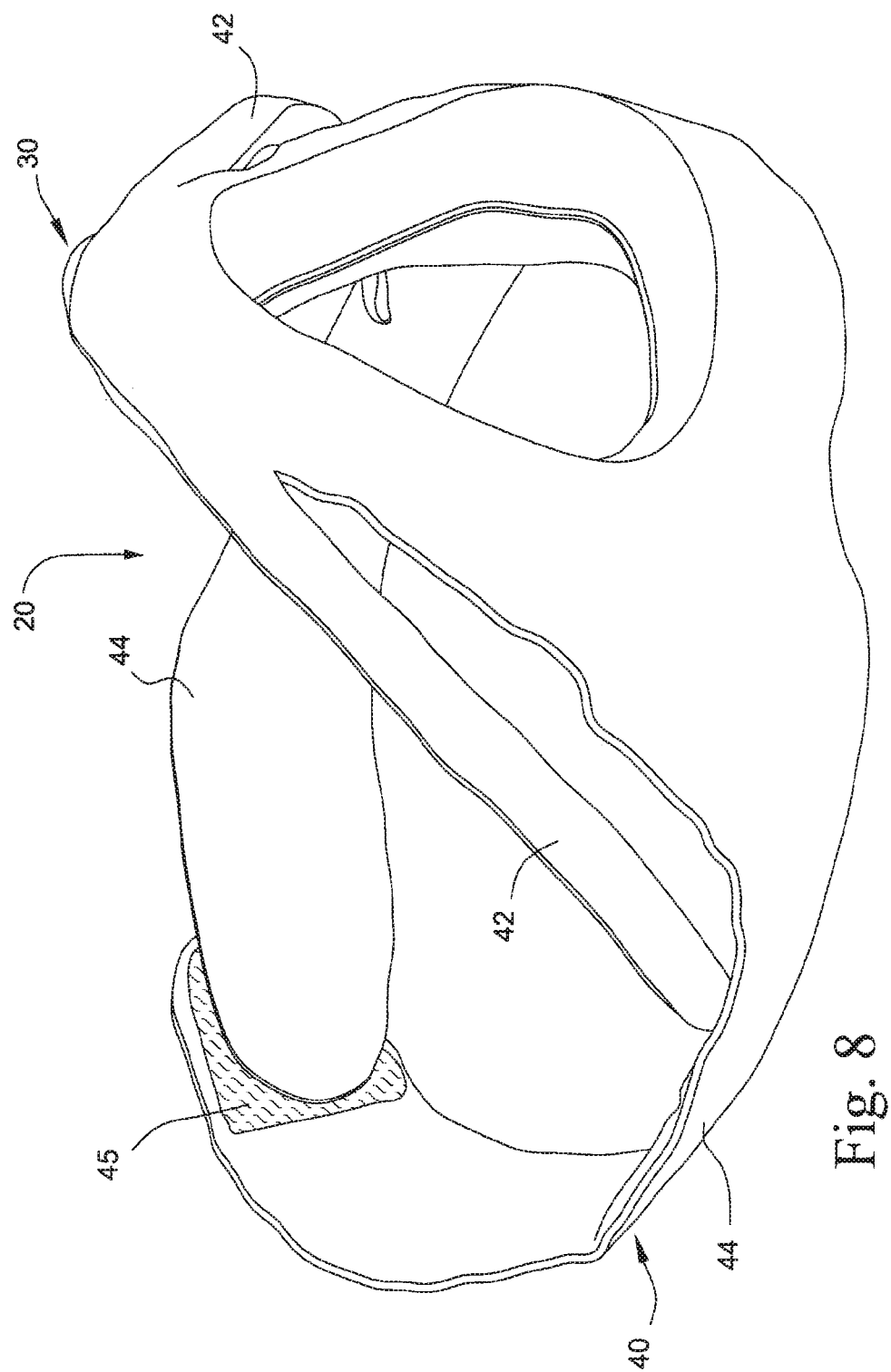
FIG. 8 is another perspective view of a headgear and cushion module of the mask system shown in FIG. 1.
Figure 9:
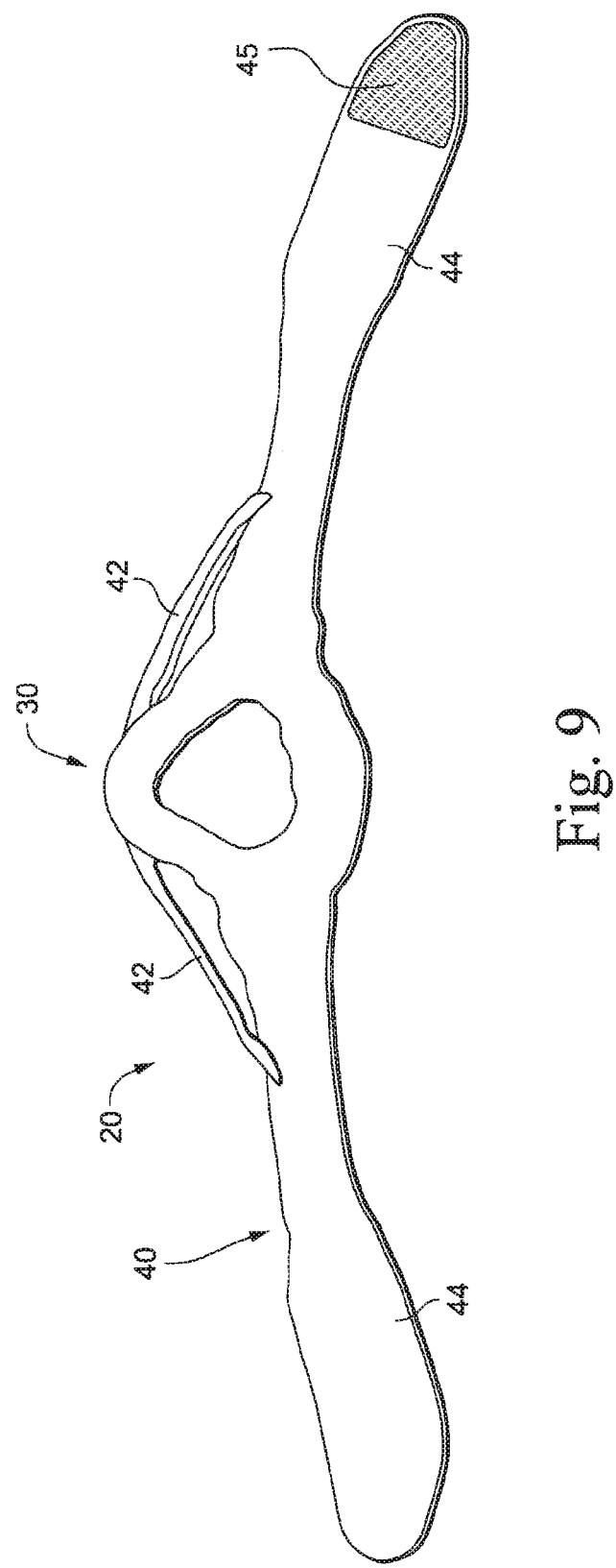
FIG. 9 is a plan-type view of a headgear and cushion module of the mask system shown in FIG. 1.

The headgear region includes headgear straps 44 that extend from either side of the cushion region 30 so as to wrap the headgear and cushion module around the head of the wearer. The headgear straps preferably connect to one another by hook and loop material 45 (e.g., see FIGS. 2, 8, and 9). Alternatively, the headgear straps may connect to each other by any other reasonable means, for example clips or buckles.

There may be at least two headgear straps. Preferably, there are four headgear straps, i.e., two upper headgear straps 42 on either side of the nose bridge region that removably attach to the lower headgear straps, and two lower headgear straps 44 that extend generally from the cheek region to the back of the patient' neck.

The upper headgear straps 42 may be thin so as to reduce visual obtrusiveness of the mask. For example, the upper headgear straps may be 1-10 mm wide. The upper headgear straps allow adjustment of the position of mask at the nasal bridge region.

The lower headgear straps 44 may be tapered at the cheek region to reduce visual obtrusiveness of the mask, e.g., see FIG. 1. For example, the cheek region of the lower headgear straps may be at least 2 mm thinner than the rest of the lower headgear straps.

Figure 14:
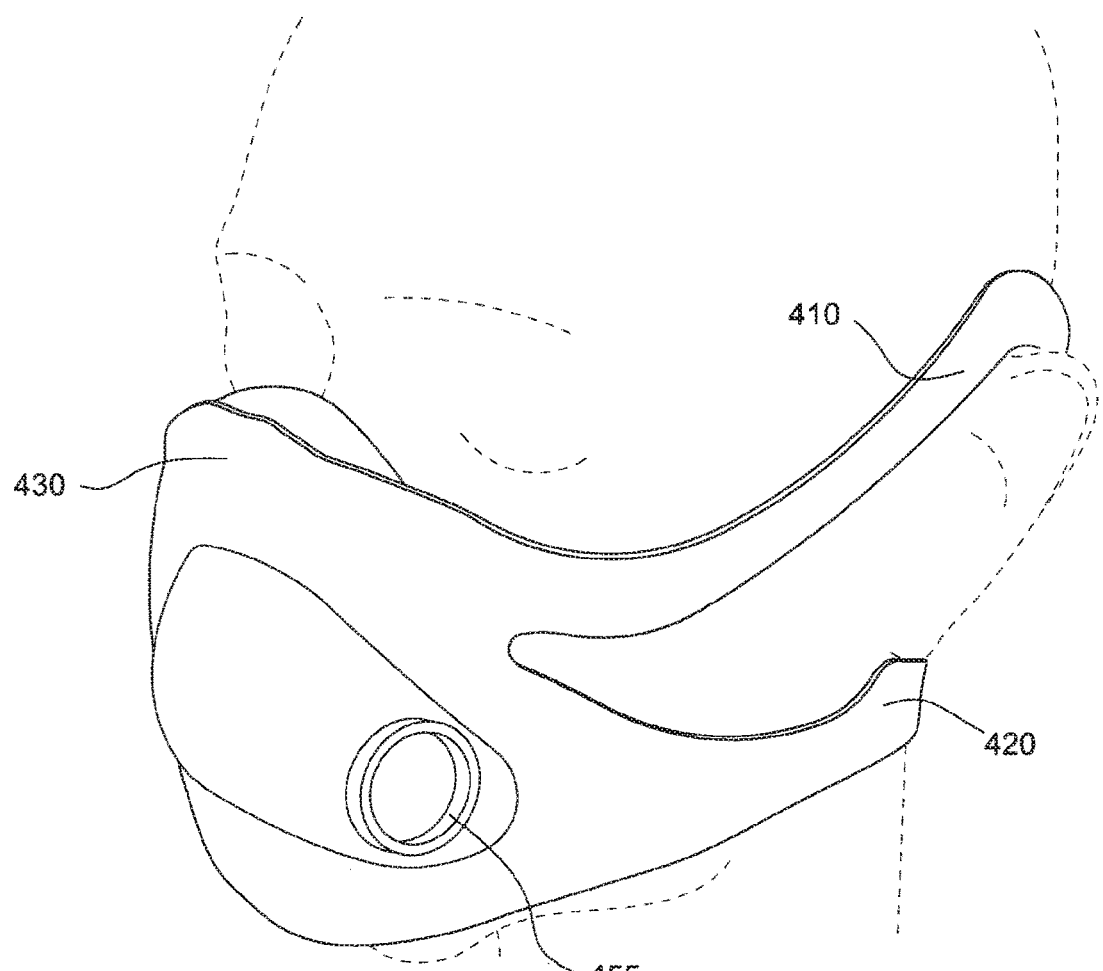
FIG. 14 is a perspective view of a mask system according to another example of the present technology, the mask system in position on a patient's head.
Figure 15:
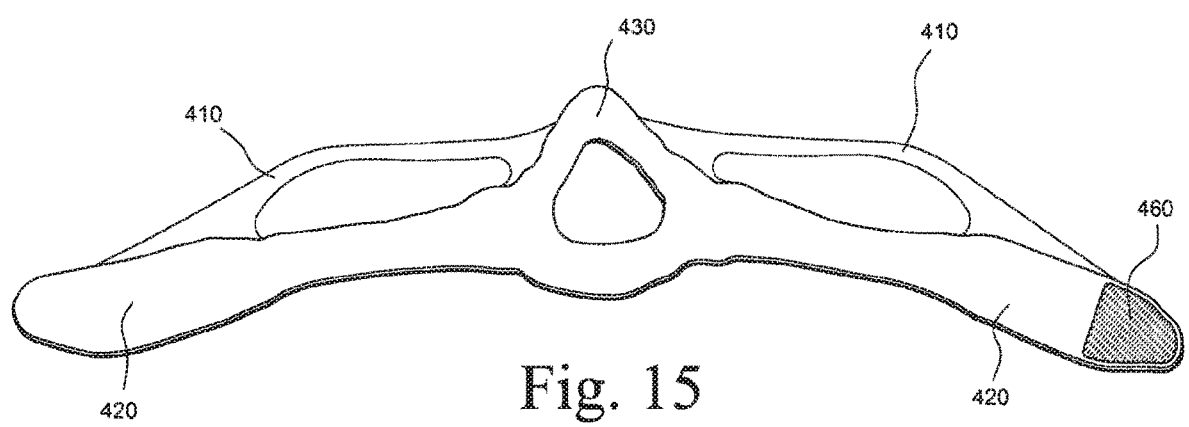
FIG. 15 is a plan-type view of a headgear and cushion module of the mask system shown in FIG. 14.

In the illustrated example as shown in FIG. 1, the headgear straps 44 are adapted to extend under the patient's ear in use. Alternative arrangements are possible, e.g., strap extending from the nose bridge region of the mask/apex, between the patient's eyes, and over the patient's head. This alternative strap arrangement may assist with seal at the nose bridge region. In another example, four straps may be provided and arranged to extend above and below the patient's ears on both sides of the patient's head in use. Such an arrangement is shown in FIGS. 14 and 15, with upper straps 410 extending over the patient's ears, and lower straps 420 extending under the patient's ears. Upper straps 410 and lower straps 420 may attach to cushion region 430, with upper straps reconnecting to lower straps 420 and lower straps 420 connectable to each other with, for example, hook and loop material 460. It should be appreciated that other headgear strap arrangements are also possible.

In an alternative example, one or more headgear straps may be formed with an air delivery tube within the fabric. For example, an air delivery tube may be contained with the fabric and communicated with the seal and frame module to deliver breathable gas to the seal and frame module.

1.3 Overall Construction

Fabric Component

The fabric may be a soft, flexible textile and may be elastic or non-elastic. Preferably, the textile may not irritate the skin. Preferably, the textile may allow the skin to breathe and/or may allow for moisture and heat to travel from the skin. For example, the textile may be moisture wicking. The textile may provide cushioning through the thickness, pile, knit, weave or fleece structure.

In an example, the fabric may be a woven, non-woven, spacer fabric, knit, polymeric weave or other suitable textile.

The fabric may be laminated or otherwise sealed so as to be air holding either completely or in part. The fabric may be selectively sealed or the entire fabric may be sealed.

Laminating

Figure 10:
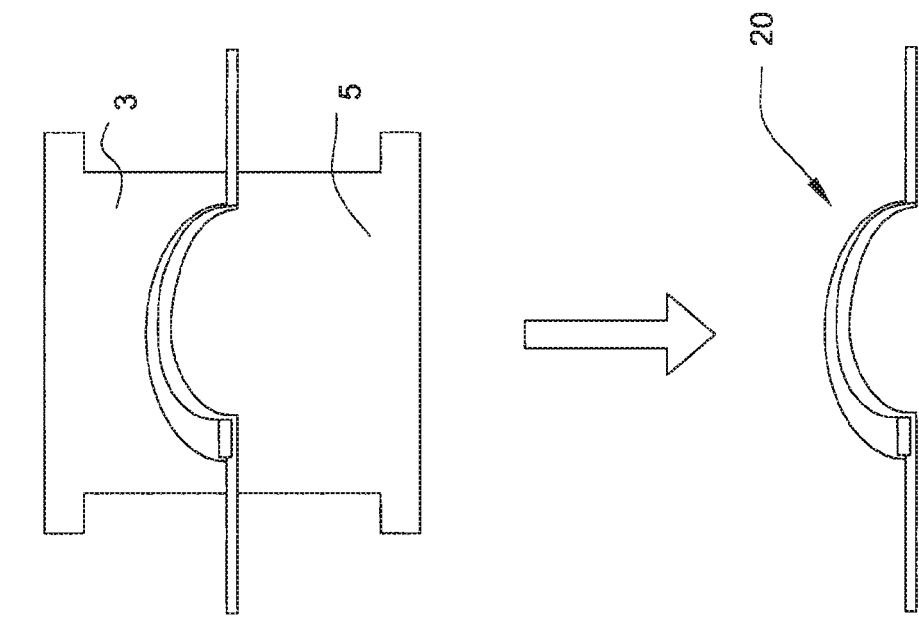
FIG. 10 is a schematic view showing a manufacturing process for making a headgear and cushion module according to an example of the present technology.
Figure 10:
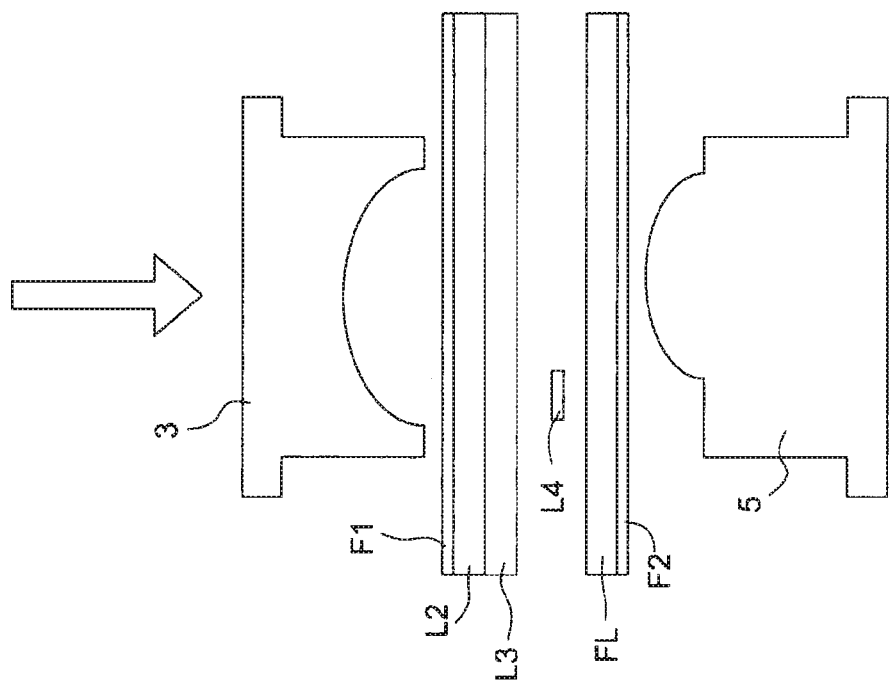

FIG. 10 illustrates a laminating process for forming the headgear and cushion module 20 according to an example of the present technology. A first fabric layer F1 is positioned for the laminating process. Preferably, this first fabric layer may have a layer of foam laminated across its length for comfort. A layer of adhesive may then be positioned over the first fabric layer. A second layer L2 is positioned over the adhesive. This second layer may be a cushioning component or a structural component. Multiple layers of cushioning and/or structural components may be positioned above this second layer. These additional layers may be rested or adhered on top of the previous layer. Preferably, a second layer is a cushioning component including a foam (e.g., Nylon/Spandex and Polyurethane foam). Preferably, a third layer L3 is cushioning component including a foam. Preferably, a fourth layer L4 is structural component (e.g., rigidizer constructed of, e.g., silicone, polypropylene, stainless steel).

A final layer of adhesive may be applied on top of the final layer. A second fabric layer F2 is then positioned on top of the adhesive. This second fabric layer may also have a foam layer FL laminated across its length (e.g., Nylon/Spandex and Polyurethane foam).

Heat and pressure (e.g., 190° C. for 80 seconds) or an ultrasonic sonotrode are then applied by a laminating tool so that the components adhere to one another. As illustrated, the tool includes an upper part 3 and a lower part 5, e.g., each part cast or machined of aluminum. The tool may be shaped to produce a curved component, for example the cushion component could be shaped to mimic the general curvature of the face. The adhesive may be a TPU adhesive. It may be in a spray, powder or strip form. It may be possible to have a foam and fabric combination where no adhesive is required, as the foam or fabric (e.g., polypropylene fabric) may melt onto the fabric or foam when heat is applied thereby fusing the foam to the fabric.

In an alternative example, flame lamination may be used to form the headgear and cushion module.

In another alternative example, fabric may be placed in a die and a stiffening material (e.g., a polymer) may be injection molded onto the fabric. The fabric may then be formed with the foam, e.g., the foam may be glued onto the injection molded polymer, the foam may be foamed onto the injection molded polymer, or the foam may be flame laminated onto the injection molded polymer.

Cutting

The shape of the headgear and cushion module may be cut before or after the laminating process. Preferably, the module will be cut by ultrasonic die cutting. Ultrasonic die cutting allows the edges of the fabric to be substantially rounded so there is less chance of facial marking and provides a more appealing look and feel. Alternatively, the module could be cut using laser cutters or die cutters. In another alternative, the fabric may be cut first, and then the foam may be foamed or otherwise provided onto the fabric.

Preferably, if the fabric has an edge from stitching, die cutting, etc., this edge may be positioned away from the patient's face, e.g., to avoid facial marking.

1.4 Shape Creation

The shape of the mask system may be influenced or controlled by selectively weakened areas or areas that may be prone to bending or flexing. For example, the headgear straps may be selectively welded through their width to create a hinge point for the headgear straps to bend about. A weld may be positioned, for example, between the cushion region and the strap to encourage the strap to bend about the weld and thereby fold inwards towards the patient's cheeks.

In an example, the headgear and cushion module may be formed with little to no pre-determined shape, i.e., the headgear and cushion module may be substantially planar. In use, the wrapping or positioning of the headgear straps may cause the cushion region to move into engagement with the patient's face, thereby shaping or bending the cushion region to match that particular patient's face shape. This is unlike typical mask systems having a rigid frame or predetermined shape of cushion that may fit a limited population due to its specified shape.

1.5 Venting

Figure 6:
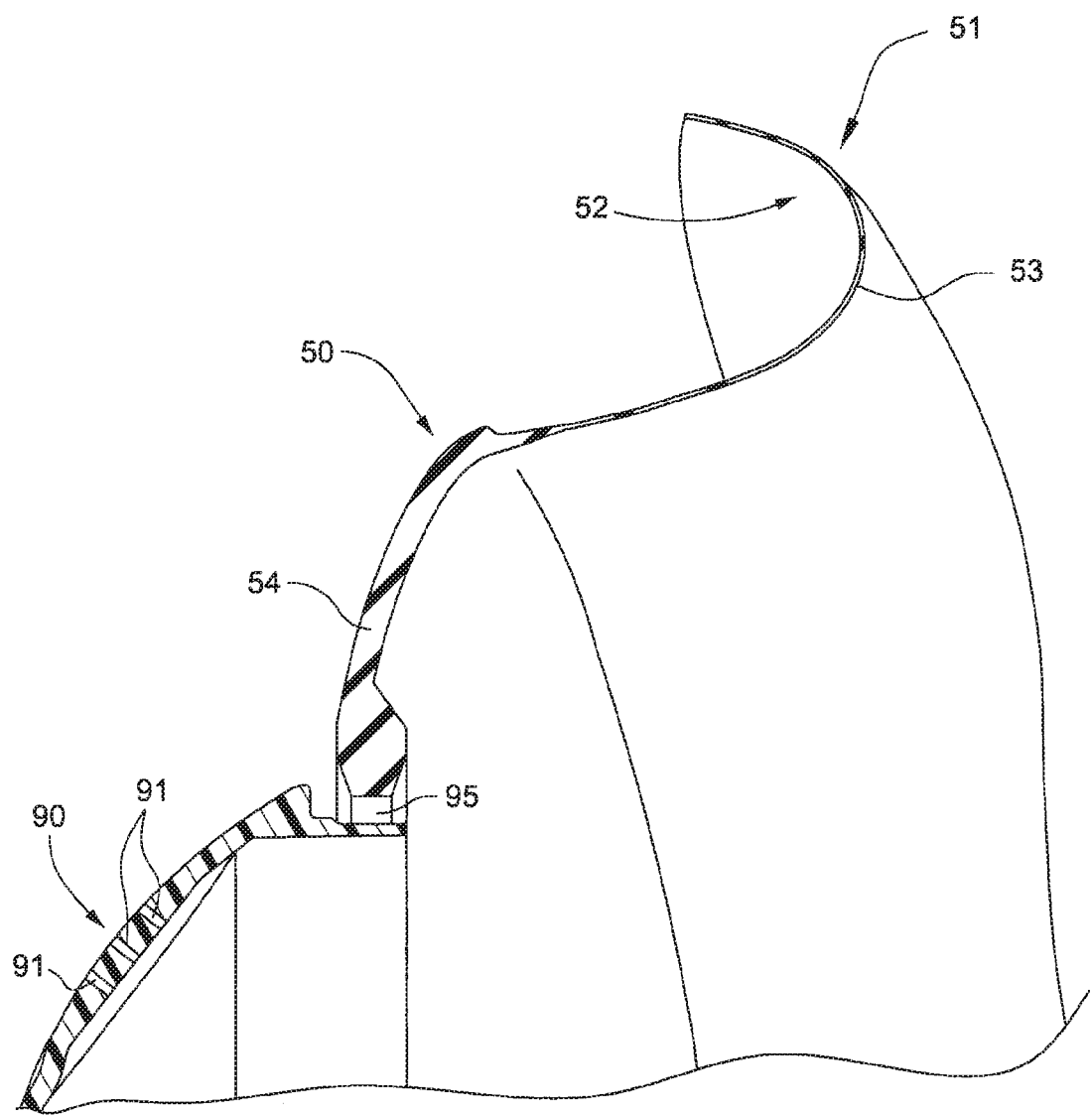
FIG. 6 is a cross-sectional view of a seal and frame module of the mask system shown in FIG. 1.
Figure 7:
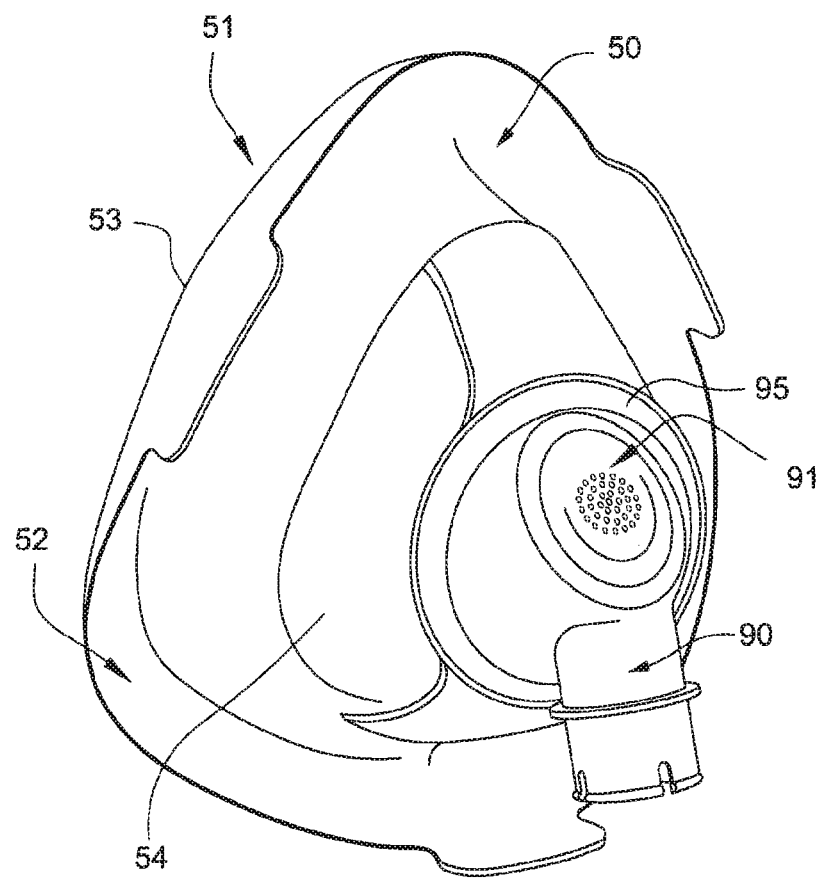
FIG. 7 is perspective view of a seal and frame module of the mask system shown in FIG. 1 provided with an elbow.

In an example, the elbow 90 may include one or more vent holes 91 (e.g., see FIGS. 6 and 7) to permit the exhaust of gases from the mask system.

In an alternative example, venting may be achieved through the fabric/foam composite material of the headgear and cushion module. For example, one or more vent holes may be cut (e.g., die cut, laser cut) or otherwise provided though the cushion region. Alternatively, the composite may be selectively coated (e.g., with a laminate) to create air permeable regions in the cushion region, e.g., one or more selected regions coated to create air impermeable regions for sealing and one or more regions uncoated to create air permeable regions for venting.

2. Seal and Frame Module

The seal and frame module 50 (shown in, for example, FIGS. 5 and 6) includes a seal portion 51 (also called the sealing membrane hereafter) and a frame portion 54. One side of the sealing membrane 51 provides a channel 52 for engaging the cushion region of the headgear and cushion module within it. The channel 52 receives the cushion region and maintains it in position. The opposite side of the sealing membrane provides a sealing surface 53 adapted to engage the patient's face in use and provide seal. The cushion region provides a reactive force to maintain the sealing surface of the sealing membrane in sealing engagement with the face of the patient. The channel is also a means of attaching the frame portion to the headgear and cushion module.

The seal and frame module is made from silicone. Preferably, the silicone may have a polished surface so that it is sticky and may therefore maintain its position on the user's face. Preferably, the seal and frame module is a single component, molded as one part or multiple parts co-molded together. The module may be a single hardness, for example 10-90 Shore A. The module may be comprised of sections of different hardness. Preferably, the sealing portion or channel may be softer than the frame portion. Preferably, the elbow connection ring 95 provided to the frame portion 54 (for connecting the elbow 90) may be harder than the frame portion 54.

Figure 5:
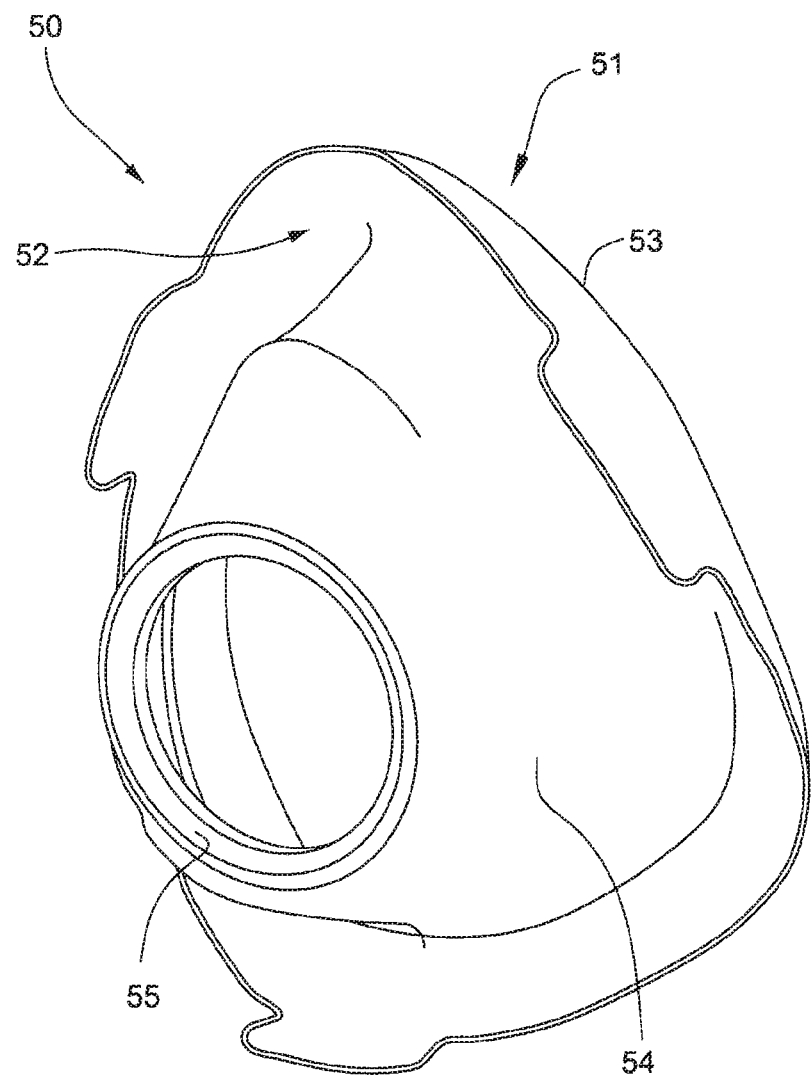
FIG. 5 is perspective view of a seal and frame module of the mask system shown in FIG. 1.

The frame portion 54 is shaped such as to create a breathing chamber or space between the mask and the patient's nose. The frame portion is also shaped so as to receive the elbow or other connection to an air delivery tube. As shown in FIG. 5, frame portion is adapted to receive an elbow or air delivery connector at receptacle 55, perpendicular and medial to the front of the frame portion. FIG. 14 shows an alternative arrangement, where the frame portion or sealed portion is adapted to receive an elbow or air delivery connector at receptacle 455 on a lateral portion of the front of the frame portion. The frame portion may be reinforced with thicker regions or with materials of higher hardness so as to maintain it's in use position. The frame portion may include a malleable wire or other such adjustment feature so that the patient can form the frame to comfortably fit on to their face in use.

Figure 19:
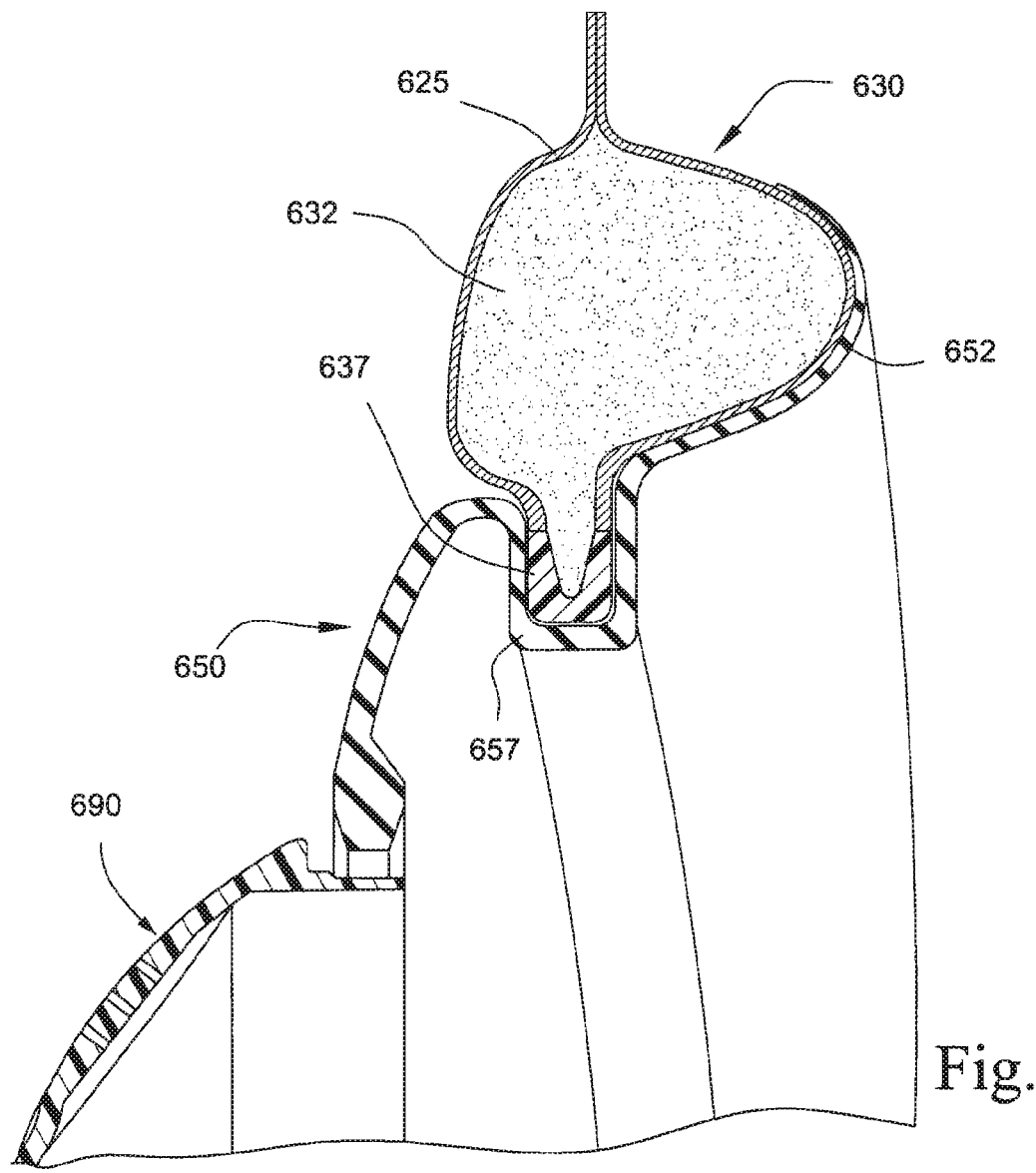
FIG. 19 is a cross-sectional view of a seal and frame module of a mask system according to another example of the present technology.

In an alternative arrangement as shown in FIG. 19, cushion portion 630 may include an outer fabric portion 625, and inner conformable portion 632 and a clip portion 637. Seal portion 650 may include a patient contacting portion 652 and a clip receiving portion 657. Clip receiving portion 657 may be adapted to receive clip portion 637 to secure cushion portion 630 in engagement with seal portion 650. Cushion portion 630 may be positioned to support patient contacting portion 652.

3. Alternative Examples

In an alternative example, the mask system may not include the seal and frame module 50 as described above. Rather, the aperture created by the headgear and cushion module 30 may be sealed or otherwise closed, e.g., by an additional piece of textile or extension of the fabric or composite of the cushion region.

Figure 11:
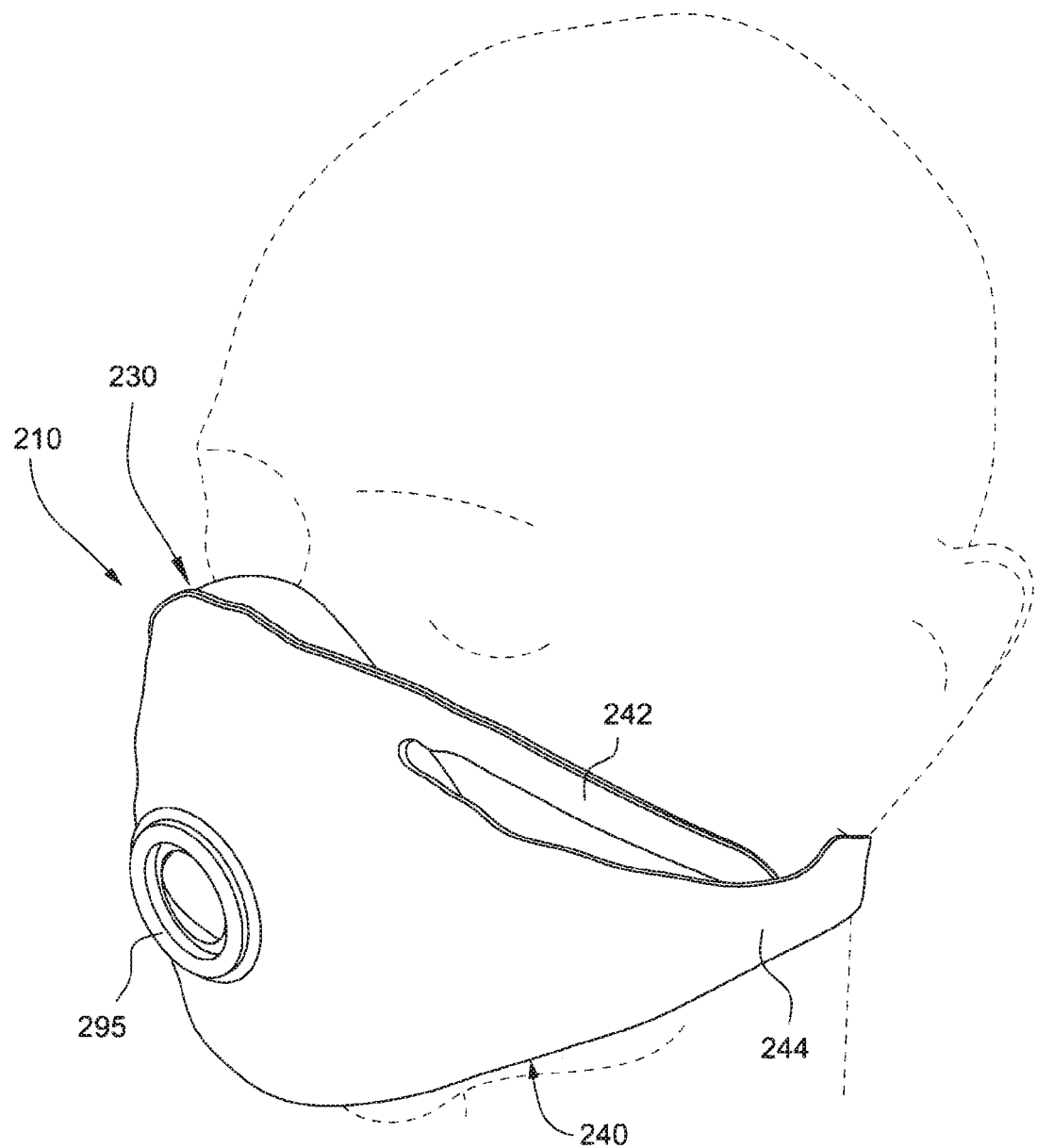
FIG. 11 is a perspective view of a mask system according to another example of the present technology, the mask system in position on a patient's head.

For example, FIG. 11 shows a mask system 210 with a one piece construction including a composite having an outer fabric layer and an inner cushioning layer within the fabric layer. As illustrated, the mask system 210 includes a cushion region 230 adapted to define a breathing chamber and form a seal with the patient's face and a headgear region 240 (with upper and lower straps 242, 244 as described above). A tube connector (e.g., connection ring 295) may be provided to the cushion region 230 for connecting an elbow or air delivery tubing.

Figure 12:
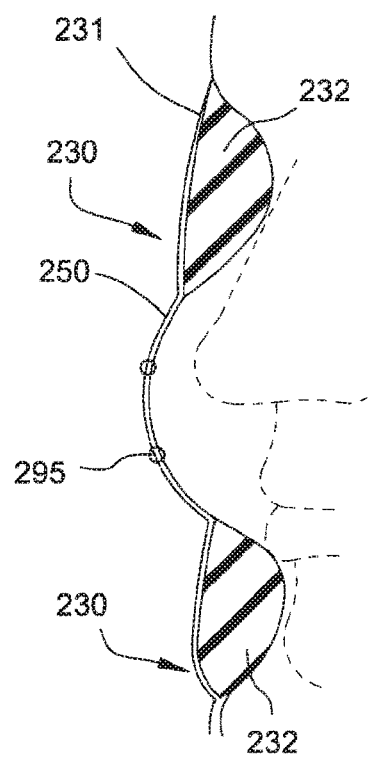
FIG. 12 is a cross-sectional view of the mask system shown in FIG. 11.

FIG. 12 shows a cross section of FIG. 11 in use. Outer fabric layer 231 and an inner cushioning layer 232 forming the cushioning region 230 are positioned about or around the patient's airways. Central portion 250 adjacent the patient's airways and defining the breathing chamber may be laminated or otherwise sealed. Connection ring 295 is positioned to receive an air delivery tube and deliver breathable gas to the sealed chamber.

Figure 16:
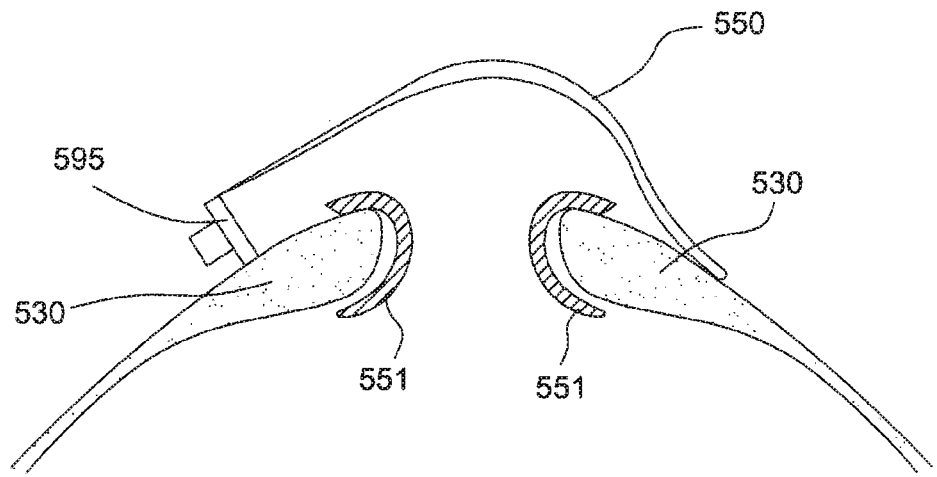
FIGS. 16 to 18 are cross-sectional views of a mask system according to another example of the present technology.
Figure 17:
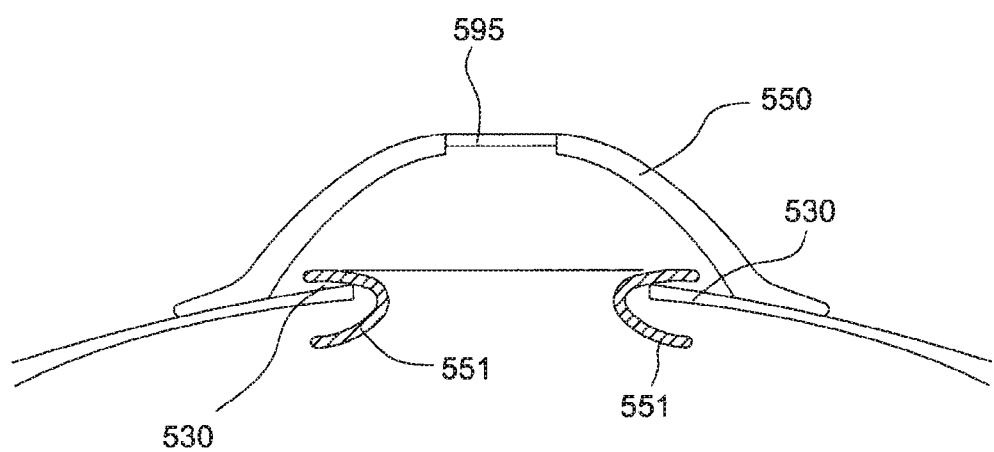
Figure 18:
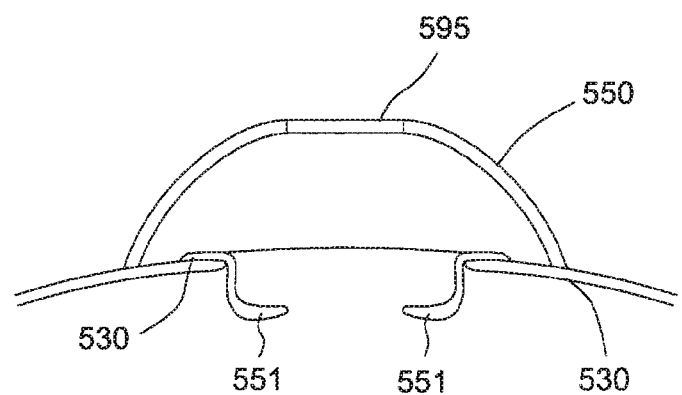

In a further alternative example, the seal portion, cushion portion and chamber portion may be formed of separate components that are connected together. As shown in FIGS. 16-18, seal portion 551 is adapted to contact the patient's face and form a seal with the patient's airways. Seal portion 551 may be formed of a silicone, TPE, TPU or other conformable polymer, or composite material including laminated textiles. Cushion portion 530 may be positioned adjacent to and supporting of seal portion 551. Cushion portion 530 may be formed of a composite for example a foam inner layer and fabric outer layer. Seal portion 551 may be adhered, fused or otherwise bonded to cushion portion 530. Alternatively, seal portion 551 may be removably attachable to cushion portion 530. Chamber portion 550 may be adapted to receive an air delivery connector via connector portion 595. Chamber portion 550 may also form the chamber through which air is delivered to the patient. Chamber portion 550 may be constructed of a polymer such as nylon, polycarbonate, polyurethane, etc. Chamber portion 550 may be welded, glued, thermoformed or otherwise attached to cushion portion 530.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface for sealed delivery of a flow of breathable gas at a continuously positive pressure with respect to ambient air pressure to an entrance to a patient's airways including at least entrance to the patient's nares for treatment of sleep disordered breathing, the patient interface comprising:

a cushion region including a breathing chamber pressurizable to a therapy pressure and a seal-forming structure adapted to form a seal with a region of the patient's face such that the flow of breathable gas at the therapy pressure is delivered to at least the entrance to the patient's nares, wherein the cushion region comprises textile around the patient's airways to form the breathing chamber and to form the seal with the region of the patient's face, wherein the cushion region comprises a central portion adjacent the patient's airways, the central portion comprising textile, and the textile of the central portion being configured and arranged to form a front wall of the breathing chamber opposite the entrance to the patient's airways, wherein at least a portion of the cushion region includes textile that is coated or sealed to create one or more air impermeable regions to form an air impermeable seal, and at least a portion of the cushion region includes textile that is uncoated or unsealed to create one or more air permeable regions to form a vent to permit venting of gases from the patient interface, and wherein the seal-forming structure includes a sealing surface along its perimeter adapted to engage with the region of the patient's face and form the seal; and at least one headgear strap including textile, the at least one headgear strap structured and arranged to extend along a side of the patient's head to support the cushion region on the patient's face, wherein the at least one headgear strap along the side of the patient's head is structured to contain a sealed air delivery passageway within the textile along the side of the patient's head, the sealed air delivery passageway arranged to communicate with a lateral portion of the cushion region to deliver breathable gas to the cushion region.

2. The patient interface according to claim 1, wherein the sealed air delivery passageway comprises an air delivery tube.

3. The patient interface according to claim 1, wherein the at least one headgear strap comprises an upper strap adapted to extend over the patient's ears.

4. The patient interface according to claim 1, wherein the at least one headgear strap comprises foam attached to the textile.

5. The patient interface according to claim 1, wherein the at least one headgear strap comprises a composite construction with the textile comprising an outer layer providing an exterior surface.

6. The patient interface according to claim 1, wherein the cushion region comprises a nasal interface.

7. The patient interface according to claim 1, wherein the cushion region comprises a full-face interface.

8. The patient interface according to claim 1, wherein the cushion region comprises nasal prongs.

9. The patient interface according to claim 1, wherein the central portion is laminated or sealed.

10. The patient interface according to claim 1, wherein the at least one headgear strap includes a one-piece construction with the cushion region.

11. The patient interface according to claim 1, further comprising a connector provided to the cushion region and adapted to communicate with the sealed air delivery passageway.

12. The patient interface according to claim 1, wherein the textile of the cushion region comprises an outer textile layer, and the cushion region further comprises an inner cushioning layer encapsulated within the outer textile layer.

13. The patient interface according to claim 12, wherein the inner cushioning layer comprises at least one layer of foam.

14. The patient interface according to claim 12, wherein the cushion region further comprises a structural component to provide structural support and stiffness to the inner cushioning layer.

15. The patient interface according to claim 1, wherein the central portion comprises the textile only.

16. The patient interface according to claim 1, wherein the textile of the cushion region comprises substantially rounded edges.

17. The patient interface according to claim 1, wherein the textile of the at least one headgear strap comprises substantially rounded edges.

18. The patient interface according to claim 1, wherein the seal-forming structure and the front wall of the breathing chamber comprise separate components that are connected to one another.

19. The patient interface according to claim 1, wherein the cushion region further comprises a structural component configured to extend outside the textile and provide connection to an external component.

20. The patient interface according to claim 19, wherein the external component is an air delivery tube.

* * * * *

UNITED STATES PATENT AND TRADEMARK OFFICE
CERTIFICATE OF CORRECTION

PATENT NO. : 10,850,058 B2
APPLICATION NO. : 15/973574
DATED : December 1, 2020
INVENTOR(S) : Gibson et al.

It is certified that error appears in the above-identified patent and that said Letters Patent is hereby corrected as shown below:

In the Claims

Column 10, Lines 4-5, In Claim 1, delete "around the patient's airways".

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*